(12) United States Patent
Doetsch et al.

(10) Patent No.: US 8,021,609 B2
(45) Date of Patent: Sep. 20, 2011

(54) STABILIZED HYDROGEN PEROXIDE

(75) Inventors: Werner Doetsch, Linz a. Rhein (DE); Otmar Woost, Bernburg (DE)

(73) Assignee: Solvay Chemicals GmbH, Hannover (DE)

( * ) Notice: Subject to any disclaimer, the term of this patent is extended or adjusted under 35 U.S.C. 154(b) by 811 days.

(21) Appl. No.: 10/804,186

(22) Filed: Mar. 19, 2004

(65) Prior Publication Data

US 2004/0247755 A1    Dec. 9, 2004

Related U.S. Application Data

(63) Continuation of application No. PCT/EP02/09284, filed on Aug. 20, 2002.

(30) Foreign Application Priority Data

Sep. 21, 2002   (DE) ................. 101 46 594

(51) Int. Cl.
*A61L 9/00* (2006.01)
*A61L 2/00* (2006.01)
*B08B 1/02* (2006.01)
*B08B 3/00* (2006.01)
*A62D 3/00* (2007.01)
*C09K 15/32* (2006.01)
*A61K 7/075* (2006.01)

(52) U.S. Cl. .................. 422/28; 422/1; 422/29; 422/32; 422/34; 422/292; 422/301; 422/302; 134/15; 134/27; 252/186; 252/186.28; 252/186.29; 252/400.24; 424/70.23; 510/469

(58) Field of Classification Search .......... 422/1, 28–29, 422/32, 34, 292, 301–302; 134/15, 27; 252/186, 252/186.28, 186.29, 400.24; 424/70.23; 510/469

See application file for complete search history.

(56) References Cited

U.S. PATENT DOCUMENTS

| | | | | |
|---|---|---|---|---|
| 3,234,140 A | * | 2/1966 | Irani | 252/186.29 |
| 3,383,174 A | * | 5/1968 | Carnine et al. | 423/273 |
| 3,903,244 A | * | 9/1975 | Winkley | 423/272 |
| 4,104,024 A | * | 8/1978 | Vogele et al. | 422/37 |
| 5,130,053 A | * | 7/1992 | Feasey et al. | 252/400.22 |
| 5,569,438 A | * | 10/1996 | Hilmersson | 422/293 |
| 5,609,821 A | * | 3/1997 | Grimberg et al. | 422/28 |

FOREIGN PATENT DOCUMENTS

| | | |
|---|---|---|
| EP | 0635273 A | 1/1995 |
| EP | 0906763 A | 4/1999 |
| FR | 2751634 A | 1/1998 |
| JP | 03-237007 A | 1/1992 |

OTHER PUBLICATIONS

"Amino-tris-methylenphosphonsaure (ATMP) und deren Salze" ZSM Website, Online! XP002226219 Retrieved from the Internet: http://www.zsm.de/german/phos/atmp.ht retrieved Jan. 3, 2003.
Ullmann's Encyclopedia of Industrial Chemistry, *Foods*, 4. Food Packaging, DOI:10.1002/143567007.a11583.pub2(2003).
Gassett et al., *Archives of Ophthalmology*, 93(6), 412-415 (1975).
Sanders, *Anti-Corrosion Method and Materials*, 44(1), 20-25 (1997).

* cited by examiner

*Primary Examiner* — Jill Warden
*Assistant Examiner* — Monzer R Chorbaji
(74) *Attorney, Agent, or Firm* — Oblon, Spivak, McClelland, Maier & Neustadt, L.L.P.

(57) ABSTRACT

A highly stabilized hydrogen peroxide useful for chemical sterilization of packaging materials in high-speed aseptic packaging plants.

20 Claims, No Drawings

STABILIZED HYDROGEN PEROXIDE

CROSS REFERENCE TO RELATED APPLICATIONS

This application is a continuation of international patent application no. PCT/EP02/09284, filed Aug. 20, 2002 designating the United States of America, and published in German as WO 03/027008 A1, the entire disclosure of which is incorporated herein by reference. Priority is claimed based on Federal Republic of Germany patent application no. DE 101 46 594.7, filed Sep. 21, 2001.

BACKGROUND OF THE INVENTION

The present invention relates to a modified hydrogen peroxide and to its use in the chemical sterilization of packaging materials. Chemical sterilization of packaging materials currently makes it possible to make foodstuffs such as milk, yoghurt or fruit juices available to the end user in simple, user-friendly packaging, without treating or impairing the respective foodstuff itself in any way. The high degree of acceptance of such user-friendly packaging results in the filling capacity of the filling machines constantly being increased, which simultaneously is often accompanied by shortening of the filling cycles.

In the chemical sterilization of packaging materials, the chemicals which can be used are limited by food regulations. Only those chemicals or mixtures which are permitted on their own or—in the case of mixtures—the individual constituents of which are permitted under food regulations are permitted to be used.

It has been shown in the past that hydrogen peroxide, as a result of its high oxidizing capacity, is a very effective germicidal medium. Consequently, hydrogen peroxide has now been used successfully for years in almost all aseptic packaging plants in the milk-processing industry and also in juice production etc.

Compared with other germicidal substances or comparable oxidizing agents, hydrogen peroxide has the great advantage of not leaving any residues other than water behind on the packaging materials as a result of the product and of the process, apart from the slight traces of stabilizer.

In the current state of the art of chemical sterilization of packaging materials, essentially two processes have become established on the market, the dip bath process and the spray process. In both these processes, hydrogen peroxide is used as a germicidal agent at elevated temperatures. The demands made on the material-specific properties of the hydrogen peroxide depend on the process in question.

Thus, for example, in the spray process the hydrogen peroxide used should for process-related reasons contain only few "inert materials", which very largely originate from the stabilizers used because in the spray process the "inert materials" result in incrustations in the evaporator or spraying section, which necessitates cleaning and ultimately reduces the filling capacity of the system.

In the dip bath process the germicidal process takes place in a bath filled with hydrogen peroxide. For this, the packaging material is passed through a temperature-controlled bath and during the later course of the process is mechanically separated from adhering hydrogen peroxide residues. As a result of the process, therefore, the hydrogen peroxide used must be more highly stabilized than the product used in the spray process referred to above.

In order to extend the useful life of the hydrogen peroxide used, foodstuff-compatible stabilizers are added to the hydrogen peroxide. It is for example known to use pyrophosphates/phosphoric acid in combination with stannates for stabilization.

The increases in filling capacity described above, with substantially unaltered dip bath geometries, are accompanied by a reduction of the residence time of the packaging material in the dip bath. In order nevertheless to maintain the sterilization effect, it is necessary to increase the operating temperature in the dip bath.

SUMMARY OF THE INVENTION

It is therefore an object of the invention to provide an improved stabilized hydrogen peroxide composition.

Another object of the invention is to provide a way of modifying hydrogen peroxide so it can be used in high-speed aseptic packaging plants at higher temperatures than have been possible in the past without shortening the filling times of the packaging plant. This can be measured by comparing the stability with the special hydrogen peroxide compositions presently used for "slower"-running packaging material sterilizing machines.

These and other object are achieved in accordance with the present invention by providing a stabilized hydrogen peroxide comprising an intimate admixture of hydrogen peroxide and from 1 to 1,000 ppm of a foodstuff-compatible phosphonic acid.

In accordance with a further aspect of the invention, the objects are achieved by providing a method of sterilizing a foodstuff packaging material comprising passing the packing material through a dip bath liquid comprising hydrogen peroxide and an effective hydrogen peroxide stabilizing amount of a foodstuff-compatible phosphonic acid.

Surprisingly, it has now been found that hydrogen peroxide can be stabilized efficiently and effectively by addition of small amounts of phosphonic acids permitted under food regulations, preferably aminotrismethylene phosphonic acid, and that a substantially lesser reduction in hydrogen peroxide concentration is observed even at temperatures of 85° C. compared with the special hydrogen peroxide types in current use in dip bath technology.

This improvement in stability behavior is not restricted only to hydrogen peroxide which has not yet been used in the process and accordingly has not picked up any contamination from the packaging material. The invention is also useful with hydrogen peroxide which as a result of the process exhibits enrichment of packaging material residues, which leads to heterogeneous decomposition. Such contaminated hydrogen peroxide treated in accordance with the invention behaves substantially more stably even at higher temperatures compared with standard quality hydrogen peroxide.

The amount of stabilizer necessary for the stabilization of hydrogen peroxide is from 200 to 500 ppm of aminotrismethylene phosphonic acid in the form of a 50%-strength aqueous solution per one liter of hydrogen peroxide.

One further surprising advantage of the hydrogen peroxide stabilized with aminotrismethylene phosphonic acid is that upon the removal of residual hydrogen peroxide following the dip bath process, even with a continuous process, no solid residues are built up on the scraper rolls.

An additional advantage lies in the preparation of the hydrogen peroxide stabilized with aminotrismethylene phosphonic acid. The necessary amount of stabilizer is mixed into a hydrogen peroxide distillate, and the addition of further stabilizers can be omitted.

The following examples are intended to illustrate the invention in further detail without limiting its scope.

EXAMPLE 1

250, 500 and 1000 μA of an aqueous 50%-strength solution of aminotrismethylene phosphonic acid (Trade name: Cublen AP1, manufactured by ZSCIMNIER & SCHWARZ, MOHSDORF GmbH & Co KG of Mohsdorf, Germany) was dissolved in commercially available hydrogen peroxide of the type D0032 from Solvay Interox. The stability values of these mixtures are reproduced in the following Table 1.

TABLE 1

| Addition of stabilizer (μl/l H$_2$O$_2$) | H$_2$O$_2$ type D0032 Stability loss (%) | H$_2$O$_2$ type D0035 Stability loss (%) |
|---|---|---|
| 0 | 38 | 23 |
| 250 | 12 | 15 |
| 500 | 5 | 11 |
| 1000 | 6 | 3 |

Stabilizer: Cublen AP1 (50%-strength solution)
Test temperature: T = 85° C.
Testing time: t = 960 min
Packaging material chips: n = 50

EXAMPLE 2

In a manner analagous to Example 1, 250, 500 and 1000 μl of an aqueous 50%-strength solution of aminotrismethylene phosphonic acid (Trade name Cublen AP1, manufactured by ZSCIMMER & SCHWARZ, MOHSDORF GmbH & Co KG of Mohsdorf, Germany) per liter of H$_2$O$_2$ was dissolved in commercially available hydrogen peroxide of the type D0032, which has been approved by the apparatus manufacturer for dip bath technology. The stability values of the resulting mixtures are reproduced in the following Table 2.

TABLE 2

| Addition of stabilizer (μl/l H$_2$O$_2$) | H$_2$O$_2$ type D0035 Stability loss (%) |
|---|---|
| 0 | 6 |
| 250 | |
| 500 | 2 |
| 1000 | 1 |

Stabilizer: Cublen AP1 (50%-strength solution)
Test temperature: T = 70° C.
Testing time: t = 960 min
Packaging material chips: n = 50

EXAMPLE 3

To measure the stability, during determination a defined number of packaging material chips having a surface area of from 55 to 60 mm$^2$ per chip were added to the samples from the foregoing Examples. To measure the stability, approximately 50 ml of the sample solution, with known concentration (W$_a$) was stored at a storage temperature of 70° C. or 85° C. over a period of 960 minutes in a glass flask. Then after the necessary correction of volume, caused by evaporated water, the hydrogen peroxide content was again determined by conventional methods for this purpose (W$_e$). The stability loss is calculated according to the formula:

$$(W_a - W_e)/W_a \times 100$$

where
W$_a$ is the initial concentration of the hydrogen peroxide used, and
W$_e$ is the final concentration of the hydrogen peroxide after 16 hours test at the respective test temperature.

The results are shown in the following Table 3:

TABLE 3

| Temperature (° C.) | Number of chips | Stability loss (%) |
|---|---|---|
| 70 | 0 | 1 |
|  | 25 | 1 |
|  | 50 | 6 |
| 85 | 0 | 1 |
|  | 25 |  |
|  | 50 | 23 |
| 96 | 0 | 1 |
|  | 25 |  |
|  | 50 | 50 |

Hydrogen peroxide type D0035
Testing time: t = 960 min

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. In a method of aseptic sterilization of a foodstuff packaging material, which comprises passing the packaging material through a dip bath liquid comprising an aseptic sterilization effective amount of hydrogen peroxide and an amount of a foodstuff-compatible hydrogen peroxide stabilizer at elevated temperature, the improvement wherein:
    (1) the hydrogen peroxide stabilizer in the dip bath liquid is a foodstuff-compatible phosphonic acid;
    (2) the amount of foodstuff-compatible phosphonic acid stabilizer in the dip bath liquid is from 200 to 500 ppm per liter of hydrogen peroxide dip bath liquid; and
    (3) the stabilized hydrogen peroxide dip bath liquid is continuously used in the method at a temperature ranging from 70° C. to 85° C. for at least 16 hours.

2. The improved method according to claim 1, wherein said foodstuff-compatible phosphonic acid is aminotrismethylene phosphonic acid.

3. The improved method according to claim 1, wherein said temperature ranges from 80 to 85° C.

4. The improved method according to claim 1, wherein said hydrogen peroxide in the dip bath liquid is a hydrogen peroxide distillate.

5. The improved method according to claim 1, wherein the stabilized hydrogen peroxide dip bath liquid is continuously used in the method for at least 16 hours with a hydrogen peroxide stability loss not exceeding 15% at a temperature of 85° C.

6. The improved method according to claim 1, wherein the stabilized hydrogen peroxide dip bath liquid is continuously used in the method for at least 16 hours with a hydrogen peroxide stability loss not exceeding 12% at a temperature of 85° C.

7. The improved method according to claim 1, wherein the stabilized hydrogen peroxide dip bath liquid is continuously used in the method for at least 16 hours with a hydrogen peroxide stability loss not exceeding 11% at a temperature of 85° C.

8. The improved method according to claim 1, wherein the stabilized hydrogen peroxide dip bath liquid is continuously used in the method for at least 16 hours with a hydrogen peroxide stability loss not exceeding 2% at a temperature of 70° C.

9. The improved method according to claim 1, wherein the stabilized hydrogen peroxide dip bath liquid is continuously used in the method for at least 16 hours with a hydrogen peroxide stability loss not exceeding 5% at a temperature of 85° C.

10. The improved method according to claim 1, wherein the concentration of hydrogen peroxide dip bath liquid is foodstuff-compatible.

11. In a method of aseptic sterilization of a foodstuff packaging material, which comprises passing the packaging material through a dip bath liquid comprising an aseptic sterilization effective amount of hydrogen peroxide and an amount of a foodstuff-compatible hydrogen peroxide stabilizer at elevated temperature, the improvement wherein:

(1) the hydrogen peroxide stabilizer in the dip bath liquid is a foodstuff-compatible phosphonic acid;

(2) the amount of foodstuff-compatible phosphonic acid stabilizer in the dip bath liquid is from 200 to 500 ppm per liter of hydrogen peroxide dip bath liquid; and (3) the stabilized hydrogen peroxide dip bath liquid is continuously used in the method at a temperature ranging from 70° C. to 85° C. for at least 16 hours without correcting for hydrogen peroxide stability loss.

12. The improved method according to claim 11, wherein said foodstuff-compatible phosphonic acid is aminotrismethylene phosphonic acid.

13. The improved method according to claim 11, wherein said temperature ranges from 80 to 85° C.

14. The improved method according to claim 11, wherein said hydrogen peroxide in the dip bath liquid is a hydrogen peroxide distillate.

15. The improved method according to claim 11, wherein the stabilized hydrogen peroxide dip bath liquid is continuously used in the method for at least 16 hours with a hydrogen peroxide stability loss not exceeding 15% at a temperature of 85° C.

16. The improved method according to claim 11, wherein the stabilized hydrogen peroxide dip bath liquid is continuously used in the method for at least 16 hours with a hydrogen peroxide stability loss not exceeding 12% at a temperature of 85° C.

17. The improved method according to claim 11, wherein the stabilized hydrogen peroxide dip bath liquid is continuously used in the method for at least 16 hours with a hydrogen peroxide stability loss not exceeding 11% at a temperature of 85° C.

18. The improved method according to claim 11, wherein the stabilized hydrogen peroxide dip bath liquid is continuously used in the method for at least 16 hours with a hydrogen peroxide stability loss not exceeding 2% at a temperature of 70° C.

19. The improved method according to claim 11, wherein the stabilized hydrogen peroxide dip bath liquid is continuously used in the method for at least 16 hours with a hydrogen peroxide stability loss not exceeding 5% at a temperature of 85° C.

20. The improved method according to claim 11, wherein the concentration of hydrogen peroxide dip bath liquid is foodstuff compatible.

* * * * *

UNITED STATES PATENT AND TRADEMARK OFFICE
CERTIFICATE OF CORRECTION

PATENT NO. : 8,021,609 B2  
APPLICATION NO. : 10/804186  
DATED : September 20, 2011  
INVENTOR(S) : Werner Doetsch et al.

Page 1 of 1

It is certified that error appears in the above-identified patent and that said Letters Patent is hereby corrected as shown below:

On the title page, Item (30), the Foreign Application Priority Data is incorrect. Item (30) should read:

-- (30) Foreign Application Priority Data

Sep. 21, 2001 (DE) ............................... 101 46 594.7 --

Signed and Sealed this
Third Day of January, 2012

David J. Kappos
*Director of the United States Patent and Trademark Office*